United States Patent [19]

Parker

[11] Patent Number: 5,743,254
[45] Date of Patent: Apr. 28, 1998

[54] OROTRACHEAL INTUBATION GUIDE

[75] Inventor: Jeffrey D. Parker, Cincinnati, Ohio

[73] Assignee: Parker Medical Limited Partnership, Cincinnati, Ohio

[21] Appl. No.: 829,737

[22] Filed: Mar. 31, 1997

Related U.S. Application Data

[63] Continuation-in-part of Ser. No. 819,289, Mar. 18, 1997, abandoned.

[51] Int. Cl.⁶ .................. A61M 16/00; A61M 5/178; A62B 9/06
[52] U.S. Cl. .................. 128/200.26; 128/207.14; 128/912; 604/160; 604/166
[58] Field of Search ............. 128/200.26, 207.14, 128/207.15, 911, 912, DIG. 26; 604/96, 158, 160, 164, 166, 170

[56] References Cited

U.S. PATENT DOCUMENTS

| | | | |
|---|---|---|---|
| 3,754,554 | 8/1973 | Felbarg | 128/351 |
| 3,756,244 | 9/1973 | Kinnear et al. | 128/351 |
| 3,802,440 | 4/1974 | Salem et al. | 128/351 |
| 3,874,377 | 4/1975 | Davidson | 128/145.5 |
| 3,908,665 | 9/1975 | Moses | 128/351 |
| 3,930,507 | 1/1976 | Berman | 128/345 |
| 3,948,255 | 4/1976 | Davidson | 128/145.5 |
| 4,068,658 | 1/1978 | Berman | 128/208 |
| 4,155,365 | 5/1979 | Boslau | 128/351 |
| 4,166,468 | 9/1979 | Hanyie | 128/351 |
| 4,167,946 | 9/1979 | Sandstrom | 128/351 |
| 4,211,234 | 7/1980 | Fisher | 128/200.26 |
| 4,231,365 | 11/1980 | Scarberry | 128/207.15 |
| 4,256,099 | 3/1981 | Dryden | 128/200.26 |
| 4,338,930 | 7/1982 | Williams | 128/200.26 |
| 4,365,625 | 12/1982 | Rind | 128/207.14 |
| 4,497,318 | 2/1985 | Donmichael | 128/202.28 |
| 4,509,514 | 4/1985 | Brain | 128/207.15 |
| 4,612,927 | 9/1986 | Kruger | 128/200.26 |
| 4,655,214 | 4/1987 | Linder | 128/207.18 |
| 4,672,960 | 6/1987 | Frankel | 128/200.26 |
| 4,683,879 | 8/1987 | Williams | 128/200.26 |
| 4,685,457 | 8/1987 | Donenfeld | 128/207.14 |
| 4,773,394 | 9/1988 | Reichstein et al. | 128/4 |
| 4,825,858 | 5/1989 | Frankel | 128/200.26 |
| 4,832,020 | 5/1989 | Augustine | 128/207.14 |
| 4,840,172 | 6/1989 | Augustine et al. | 128/207.14 |
| 4,919,126 | 4/1990 | Baildon | 128/207.14 |
| 5,038,766 | 8/1991 | Parker | 128/200.26 |
| 5,042,469 | 8/1991 | Augustine | 128/200.26 |
| 5,203,320 | 4/1993 | Augustine | 128/10 |
| 5,339,805 | 8/1994 | Parker | 128/200.26 |

FOREIGN PATENT DOCUMENTS

| | | | |
|---|---|---|---|
| 289098 | of 0000 | Argentina . | |
| 0233761 | 8/1987 | European Pat. Off. | A61B 1/26 |
| 0234847 | 9/1987 | European Pat. Off. | A61B 1/26 |
| 2489686 | 9/1981 | France | A61B 1/26 |
| 1535060 | 12/1978 | United Kingdom | A61M 25/00 |
| 2137096 | 10/1984 | United Kingdom . | |
| 2205499 | 12/1988 | United Kingdom | A61M 16/04 |
| 2229367 | 9/1990 | United Kingdom | A61M 16/00 |

OTHER PUBLICATIONS

Bleyer, J. Mount, *Some Practical Hints in Connection with Intubation of the Larynx, and a Resume of 206 Cases Operated on From 1886 to 1888*, N.Y. Med. Jour., Feb. 2, 1889, pp. 122–125.

(List continued on next page.)

*Primary Examiner*—Kimberly L. Asher
*Attorney, Agent, or Firm*—Wood, Herron & Evans, L.L.P.

[57] ABSTRACT

A blind intubation guide (10) including a tube-receiving space (46) with a tube-supporting spout (50) which effectively overhangs the epiglottis (90) so as to prevent an orotracheal tube (60) from catching thereon as such tube (60) is advanced through the guide (10). A guide wall (42), which aims the tube (60) into the laryngeal opening (82) and has an upper edge below the level of the junction of the spout (50) and an aft member (16) and a support member (30) of the guide, cooperates with a free edge (52) of the spout (50) to rotate the tube (60) into position for advancement into the laryngeal opening (82) and the trachea (96).

30 Claims, 4 Drawing Sheets

OTHER PUBLICATIONS

Brain, A.I.J., *Three Cases of Difficult Intubation Overcome by the Laryngeal Mask Airway*, Anaesthesia, 1985, vol. 40, pp. 353–355.

Liban, J.B. et al., *A New Blade for Endotrachael Intubation*, British Journal of Anesthesia, vol. 49, pp. 1279–1280 (1977).

Bleyer, J. Mount, *Tongue and Larynx Tractor, for the Performance of Forced Laryngoscopy in Children. Mouth–Gag and Cupped–Out Intubation–Tube, with False Metal Epiglottis Attachment*, Archives of Pediatrics, pp. 597–599 (Oct. 1888).

Leroy, *Recherches Sur L'Asphyxie*, 7 J. de Physiologique, 45, 65, 1827.

Knapp, *A Director for the Stomach Tube*, Med. Record N.Y., 322, Aug. 29, 1896.

*Understanding Anesthesia Equipment*, pp. 342–343 and 346–349.

*Fundamentals of Tracheal Intubation*, pp. 74–76 and FIGS. 4–9 at p. 56.

Machida, *The Next Generation Nasopharyngo–Laryngoscopes*.

*Rusch Super Safety Clear Endotracheal Tubes*.

*Anesthesiology Review*, p. 24, vol. III, No. 1.

Brain, A.I.J., *The Laryngeal Mask—A New Concept in Airway Management*, Br. J. Anaesth. (1983), vol. 55, pp. 801–805.

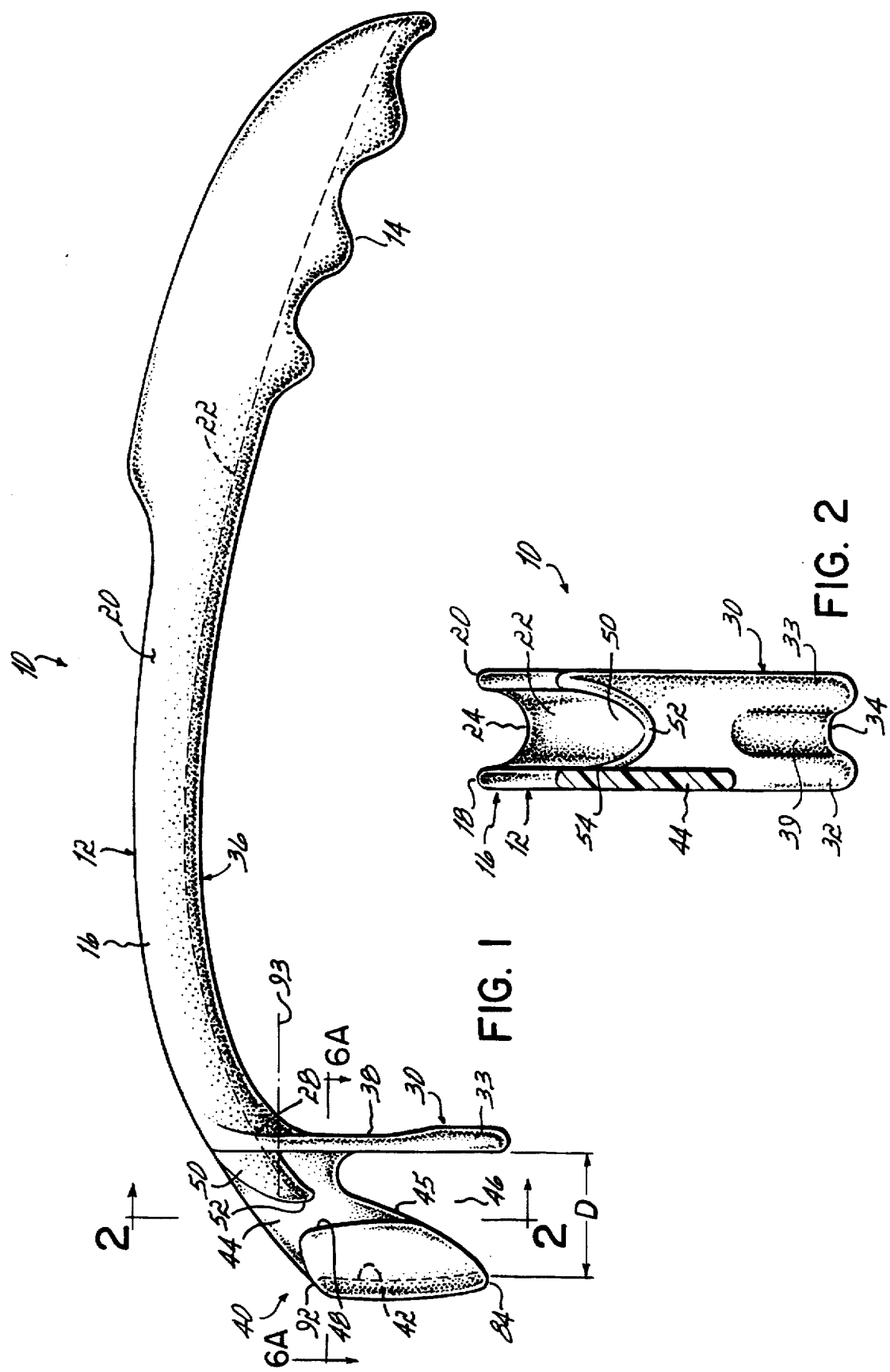

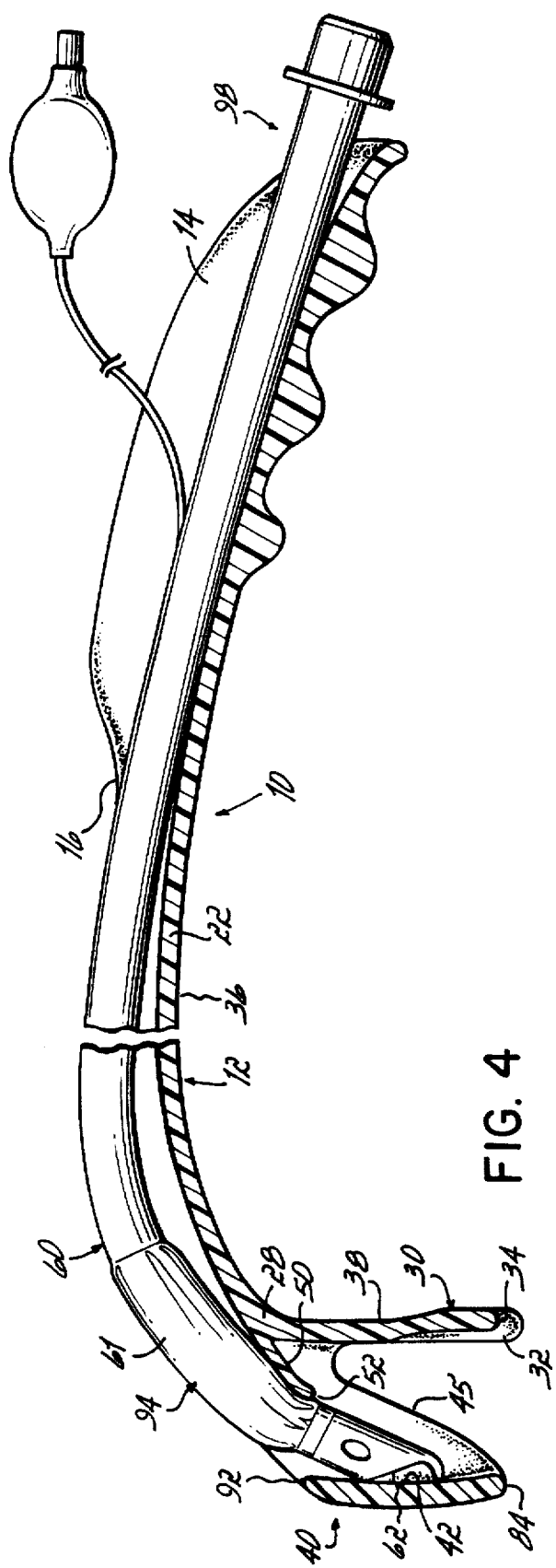
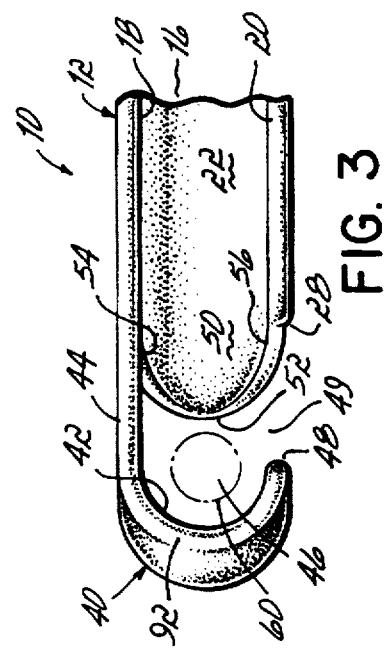
FIG. 3
FIG. 4

OROTRACHEAL INTUBATION GUIDE

RELATED APPLICATIONS

The present application is a continuation-in-part of my application entitled "Orotracheal Intubation Guide", Ser. No. 08/819,289, filed Mar. 18, 1997, now abandoned, the disclosure of which is incorporated herein in its entirety by reference.

BACKGROUND OF THE INVENTION

I. Field of the Invention

The present invention relates to orotracheal intubation guides and more particularly to blind intubation guides for insertion of an orotracheal tube into a patient's trachea.

II. Description of Prior Art

When a patient stops breathing, it is imperative that effective ventilation be instituted as soon as possible. Ventilation is best accomplished by forcing air through an orotracheal tube inserted through the mouth and laryngeal opening and into the trachea. A commonly employed method of orotracheal intubation relies on a blade laryngoscope by which to visualize the laryngeal opening so as to facilitate insertion of the tube. Intubation with the blade laryngoscope presents significant difficulties and risks. In addition to possible injury or trauma to the patient in the utilization of the blade laryngoscope, it is not uncommon for the orotracheal tube to be accidentally inserted into anatomical spaces surrounding the larynx, such as the closely adjacent esophagus. Such misintubation, if not quickly recognized and corrected, may have fatal consequences.

Another approach to intubation is so-called blind intubation in which a guide device is inserted into the throat to guide the orotracheal tube into the laryngeal opening without requiring visualization of the laryngeal opening. Such devices might reduce the injury and trauma to patients that occurs with use of blade laryngoscopes, but they usually have no means to prevent misintubation. I have developed several blind intubation guides which not only minimize injury and trauma in use, but also substantially reduce the risk of misintubation. One particularly advantageous blind intubation guide is described in my U.S. Pat. No. 5,339,805, the disclosure of which is incorporated herein in its entirety.

The guide of my '805 patent has an aft portion or member with a floor to support the orotracheal tube during its passage through the mouth. The aft portion has a generally horizontal orientation with the floor having an arc thereto following the arc of the tongue. The floor continues down into a generally vertical support portion which is designed to mate with the valleculae at the back of the tongue and in front of the epiglottis. The underside of the aft member functions as a tongue-depressor to hold the tongue down against the floor of the mouth. As also shown in my '805 patent, the guide may have an upper wall or roof that parallels the floor and merges into a generally vertically oriented guide wall spaced forwardly of the support portion and designed to be positioned at the back of the throat with a lower edge that seats adjacent to the posterior edge of the laryngeal opening. The orotracheal tube follows a path defined between the roof and the floor such that the orotracheal tube will bear against the guide wall and slide therealong into the laryngeal opening and trachea. To that end, the lower edge of the guide wall sits adjacent to the posterior wall of the laryngeal opening so as to be effectively contiguous with that wall and to effectively define an upward extension thereof along which the tube progresses. As a consequence, the guide wall does permit deviation by the tube from a trajectory which leads the tube into the laryngeal opening. Intubation may thus be accomplished easily and safely and without substantial risk of injuries and or misintubation which too commonly occur with the use of the blade laryngoscope and previous blind intubation guide devices.

While the intubation guide of my '805 patent is thus a significant improvement over the blade laryngoscope, as well as earlier attempts at blind intubation, it appears that, in some instances, the orotracheal tube may catch on the epiglottis as the tube is advanced beyond the support portion of the guide toward the guide wall. When that occurs, the tube may push or drag the epiglottis over the laryngeal opening thereby blocking that opening and thwarting the effort to direct the tube into the laryngeal opening.

SUMMARY OF THE INVENTION

The present invention provides an improved blind intubation guide which prevents the orotracheal tube from catching on the epiglottis. To this end, and in accordance with principles of the present invention, the intubation guide is provided with an extended tube-supporting surface, such as a spout or extension of the floor, which continues in a generally horizontal orientation beyond the support portion and toward the guide wall to thus overhang at least a portion of the space between the support portion and the guide wall. In this manner, when the guide is seated in the throat with the support member at the back of the tongue, the spout effectively overhangs the epiglottis such that when the orotracheal tube is advanced from the aft member along the spout toward the guide wall, the tube will pass over and beyond the epiglottis and so will not catch on, push, or drag the epiglottis.

The spout need not necessarily actually overhang the epiglottis, so long as the spout extends above the level of the epiglottis and functionally overhangs the epiglottis, such that a tube advanced along the upper surface of the spout will pass over and beyond the top of the epiglottis, so as to provide an epiglottis-free tube trajectory from the aft member to the guide wall.

The guide member includes an aft, tongue-depressing portion which has a generally horizontal orientation, and a generally vertically disposed support portion or member which mates, for example, with the vallecular depressions behind the tongue, and is connected to the aft member at the distal end thereof The guide wall is likewise generally vertically oriented and spaced from the support member a fixed distance so as to define a tube-receiving space therebetween. The spout advantageously extends from the aft member distal end into the tube-receiving space toward the guide wall, the forward edge of the spout approaching the guide wall no closer than the outer diameter of the cuff of the largest tube intended to be advanced through the tube-receiving space. The spout may be viewed as a continuation of the floor of the aft member which creates an overhanging eave that terminates in a free edge over which the orotracheal tube may rotate from a relatively horizontal position to a more vertical position as the tube tip passes along the guide wall. The spout may project slightly downwardly and advantageously has a generally concave cross-section to cooperate with the contour of the tube periphery and confine its trajectory toward the guide wall. The guide wall may be held to the support member and aft member by a single side arm, and the guide may be removed from the tube by passing the tube laterally through an opening opposite the side arm. A lateral or side edge of the spout is adjacent to, and advantageously interconnected with, the side arm.

It appears that in order to slide easily into the laryngeal opening, the tube, after passing over the epiglottis, needs to quickly rotate into a more vertical orientation than is possible to achieve with some prior art devices. For example, the roof in the guide of my '805 patent tends to confine the tube to a controlled arcuate path which is too horizontal and which limits the ability of the tube to arch upward from the floor of the device as desired. The present guide overcomes this problem in two ways. First, it eliminates the upper wall or roof of the guide, at least in the area of the guide wall and over the tube-receiving space between the guide wall and the support member. To this end, and in accordance with this further aspect of my present invention, the guide wall has an upper edge which is below the level of the junction of the aft member, support member, and spout, such that there is no roof above the tube-receiving space to limit upward flexure or a vertical orientation of the tube. Second, the guide wall and the free edge of the spout combine to partially rotate the advancing tube into the desired orientation. As the distal tip of the tube is advanced along the guide wall, the medial and proximal portions of the tube are forced to partially rotate around the free edge of the spout, causing those portions of the tube to rise upwardly from the generally horizontal floor of the aft member into a more vertical orientation, thereby allowing the tube to slide more easily along the relatively vertical pathway between the guide wall and spout free edge into the laryngeal opening. The free edge of the spout is rounded to facilitate this rotation.

By virtue of the foregoing, there is thus provided a blind intubation guide that may be used to reliably and safely place an orotracheal tube into a patient's trachea without catching on, pushing, or dragging the epiglottis and with an effective trajectory to the tube. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate an embodiment of the invention and, together with the general description of the invention given above and the detailed description of the embodiment given below, serve to explain the principles of the present invention.

FIG. 1 is a left side elevational view of a blind intubation guide in accordance with the principles of the present invention;

FIG. 2 is a view taken along line 2—2 of FIG. 1;

FIG. 3 is a partial, top view of the guide of FIG. 1;

FIG. 4 is a partially broken-away, left side elevational view of the guide of FIG. 1 showing its use with an orotracheal tube;

DETAILED DESCRIPTION OF THE DRAWINGS

Figure 5:
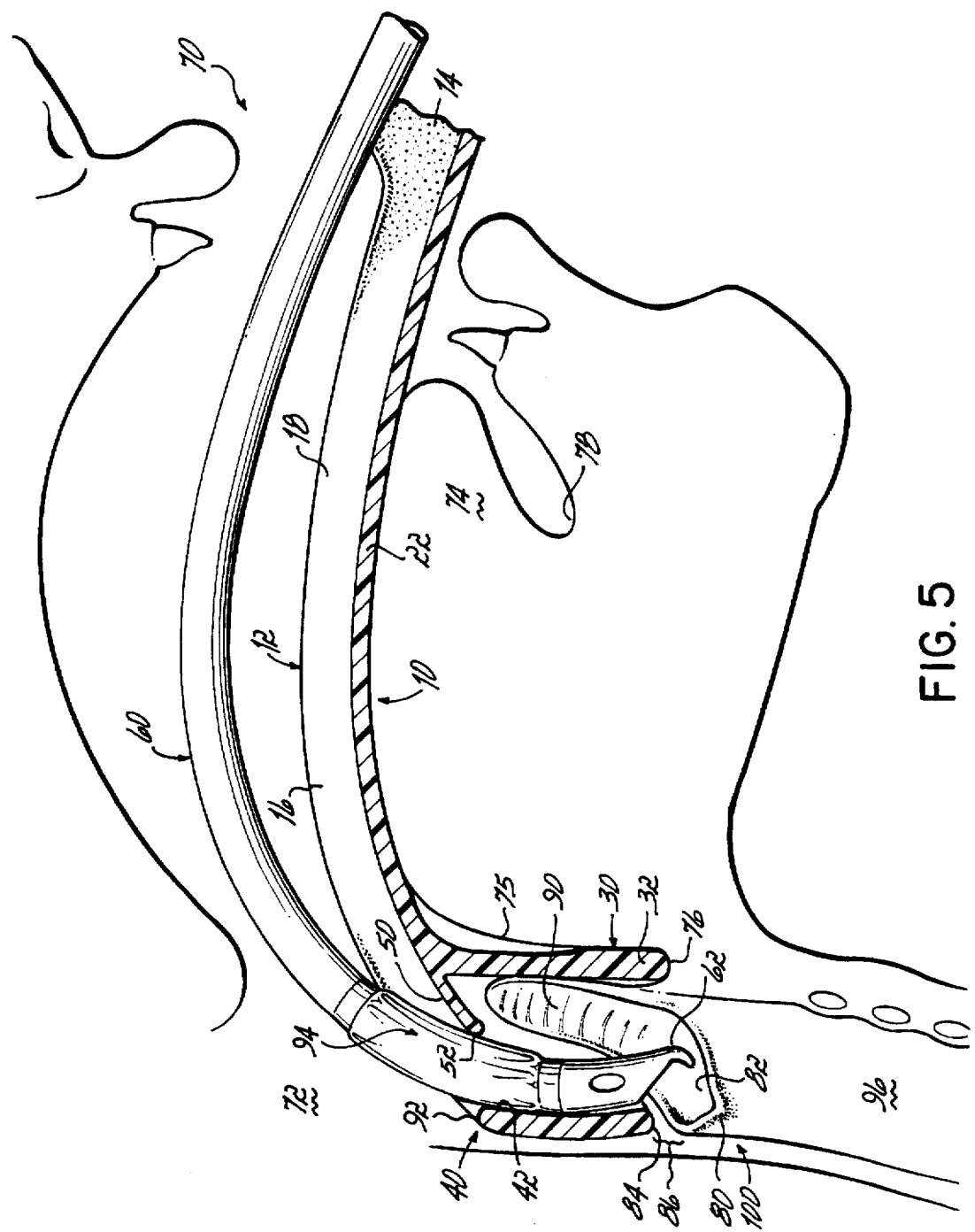
FIG. 5 is a schematic illustration, partially cut way, showing the guide of FIG. 1 positioned in the throat with the orotracheal tube advancing along the guide wall for purposes of explaining the principles of the present invention.

With reference to FIG. 1, there is shown a blind intubation guide 10, injection molded as a single piece of plastic (such as polyethylene, polypropylene, or ABS) and constructed in accordance with the principles of the present invention. Guide 10 includes a main member 12 having a proximal handle portion 14 and an aft tongue depressing portion or member 16. As may be seen in greater detail in FIG. 2, aft portion 16 has a generally U-shaped cross-section or groove having left and right side walls 18 and 20 and floor 22, the latter of which extends in a generally horizontal, albeit somewhat arcuate, orientation as depicted in FIG. 1. Side walls 18, 20 and floor 22 may extend or merge with handle portion 14 as desired. Depending in a generally vertical orientation from the distal end 28 of aft member 16 is a support portion or member 30. Support portion 30 terminates in a pair of spaced-apart legs 32, 33 with a medial notch 34 therebetween. The underside surface 36 of aft member 16 merges continuously into backside 38 of support portion 30 and defines a tongue-depressing surface of guide 10. The front side 39 of support portion 30 may be slightly concave in cross-section.

Spaced forwardly of support portion 30 is tube tip guide portion 40. Tube tip guide portion 40 has a generally vertically disposed inner guide wall surface 42 which, as seen from the top in FIG. 3, has a generally concave cross-section, with portion 40 being about 2 to 5 mm thick. Tube tip guide portion 40 is connected to support portion 30 and to aft member 16 by a single side arm 44 which has an arched lower edge 45. Arm 44 spaces support portion 30 and guide wall 42 apart to define a tube-receiving space 46 therebetween. The free vertical edge 48 of tube tip guide portion 40 is spaced opposite leg 33 of support portion 30 to define a tube-removal slot 49 therebetween. The width of slot 49 must be no more than 2–3 mm less than the outer diameter of the largest orotracheal tubes 60 (see FIG. 4) which are intended to be passed through that slot, in order for such tube to be laterally removable from space 46 through slot 49.

Guide 10 further includes an extended tube-support 50 terminating in a free distal edge 52 which extends into space 46 between support portion 30 and guide wall 42 so as to effectively define a generally horizontal, but somewhat downwardly sloping, continuation of floor 22 of aft member 16. The distance between edge 52 and guide wall 42 must be at least slightly larger than the outer diameter of the cuff 61 (FIG. 4) of the largest orotracheal tube 60 which is intended to be passed therethrough, in order to permit easy sliding of the tube therebetween. Tube-support surface 50 may be viewed as a spout that creates an overhanging eave in space 46. As seen in FIG. 2, spout 50 has a generally concave cross-section. The lateral, left side edge 54 of spout 50 is adjacent to, and advantageously interconnected with, side arm 44 (see FIG. 3), with the right side edge 56 exposed through slot 49.

The upper aspect of member 12 is adapted to receive and support an endotracheal tube 60 (referred to as an orotracheal tube when it is inserted through the mouth as intended here) therein as seen in FIG. 4. To this end, tube 60 may fit within the U-shaped cross-section of member 12 such that distal tip 62 of tube 60 can be advanced beyond spout 50 and beyond free edge 52 toward guide wall 42 to impact and bear thereagainst. With tube 60 pre-loaded into member 12 (or before placing tube 60 into member 12, if desired), guide 10 may be inserted through a patient's mouth 70 and into the throat 72. To this end, and with reference to FIG. 5, while depressing tongue 74 and/or pulling it out of mouth 70, guide 10 is inserted such that legs 32 and 33 of support portion 30 ride over tongue 74, until support portion 30 comes to rest at the back 75 of tongue 74 with legs 32, 33 setting into valleculae 76 (only one shown) behind tongue 74. In this position, aft member 16 is supported over tongue 74 by support member 30 while also serving to keep tongue 74 down against the floor 78 of mouth 70. Also when support portion 30 mates with the anatomy of the throat 72 as above-described, guide wall 42 is situated at the back of the throat 72 in an orientation that effectively defines an upward continuation of the posterior edge 80 of the laryngeal opening 82. More particularly, the lowermost edge 84 of guide wall 42 is generally adjacent to or contiguous with the posterior edge 80 of laryngeal opening 82 so as to prevent tube tip 62 from passing between guide wall 42 and laryngeal edge 80 into the esophagus 100 or other anatomical spaces outside the laryngeal opening. As may be seen in FIG. 5, lower edge 84 of guide wall 42 need not necessarily touch the posterior edge 80 of laryngeal opening 82 so long as they are functionally contiguous such that the gap 86 is dimensionally and/or angularly inaccessible to tube tip 62 so as to provide a pathway from tube-receiving space 46 exclusively into laryngeal opening 82 and trachea 96.

With guide 10 seated in the throat of the human or animal patient, the patient's epiglottis 90 projects generally upwardly along front side 39 of support portion 30, and below the level of the overhanging eave defined by spout 50. Downward pressure applied to the valleculae from aft member 16 via legs 32,33 and medial notch 34, and/or traction applied to the back of the tongue via aft member 16, will cause the epiglottis 90 to assume a more upright position closer to surface 39 below spout 50. As a consequence, orotracheal tube 60 may pass beyond free edge 52 of spout 50 and toward guide wall 42 without encountering epiglottis 90. When tip 62 contacts and beings to slide downward along guide wall 42, the medial portion 94 of tube 60 above spout edge 52 is forced to rotate thereabout and to arch upward from its generally horizontal orientation along floor 22 and spout 50 (as shown in FIG. 5). This gives the portion of the tube in space 46 a more vertical orientation, facilitating its passage downward past gap 86 and into and through laryngeal opening 82. To accommodate this more vertical positioning of tube 60, space 46 between guide wall 42 and support member 30 is unobstructed from above (other than by spout 50), and upper edge 92 of tube tip guide portion 40 is situated, advantageously, below the level of the junction 28 of after member 16, support portion 30, and spout 50 (FIG. 1), i.e., below horizontal plane 93 defined thereat.

Figure 6A:
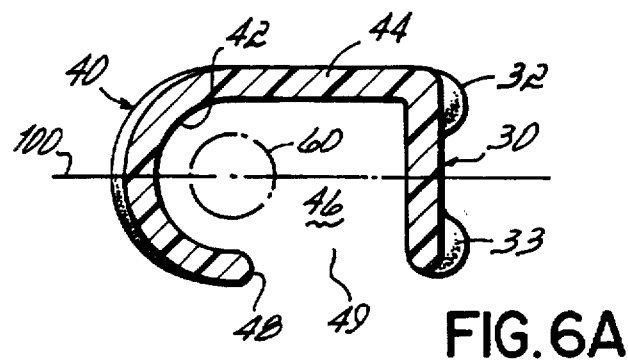
FIG. 6A is a cross-sectional view taken along line 6—6 of FIG. 1.
Figure 6B:
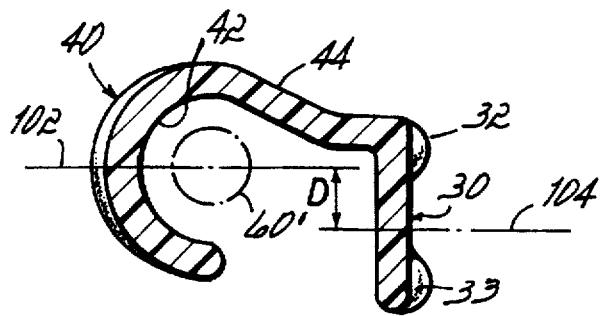
FIG. 6B is a view similar to FIG. 6A showing an offset guide wall alternative embodiment of the invention.
Figure 6C:
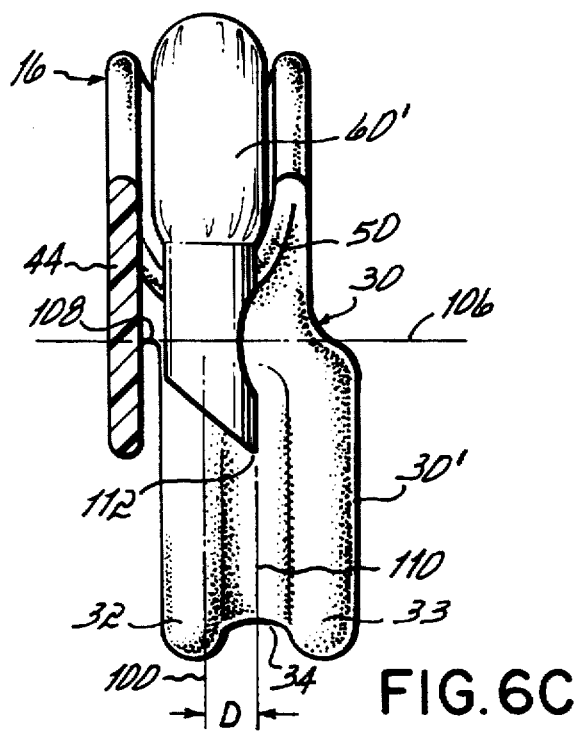
FIG. 6C is a view similar to FIG. 2 but with a standard orotracheal tube in place and showing an alternative embodiment of the invention, including an offset support member.

Guide 10 may have a non-offset guide wall 42 and support member 30, an offset guide wall 42, or an offset support member 30 as will now be described with reference to FIGS. 6A, 6B and 6C, respectively. As seen in FIG. 6A, guide wall 42 and support member 30 are not laterally offset from one another (or from the midline of aft member 16). Instead, guide wall 42 and member 30 are in confronting relationship such that a generally vertical plane 100 bisecting guide wall 42 would also bisect support portion 30. In this version, plane 100 also bisects tube 60 as well. Where a typical side-facing beveled tube 60' is to be employed with guide 10, it may be desirable to laterally offset guide wall 42 with respect to support member 30 so as to align the chisel point (not shown) of the tube with the anterior-posterior midline of laryngeal opening 82. To this end, either guide wall 42 may be shifted relative to the rest of guide device 10, or support member 30 may be shifted. The former is shown in FIG. 6B wherein arm 44 and spout 50 (not shown in FIG. 6B) are shifted or contoured so that guide wall 42 is offset to the right from the position shown in FIG. 6A. With the offset, a first generally vertical plane 102 bisecting guide wall 42 does not bisect support member 30. Instead, a second generally vertical plane 104 bisecting member 30 (and coincident with the midline of aft member 16) is generally parallel to, but spaced away a distance D from, plane 102. The distance D is advantageously equal to about one-half the outer diameter of tube 60', with plane 102 also bisecting tube 60'. Alternatively, with guide wall 42 held in position relative to aft member 16 (as shown in FIG. 6A) such that vertical plane 100 is coincident with the midline of aft member 16 (not shown in FIG. 6A), support member 30 may be shifted with respect to guide wall 42 and the midline of aft member 16 as seen in FIG. 6C. In the embodiment shown in FIG. 6C, the lower aspect 30' of support member 30 below a horizontal plane intersecting upper edge 108 of arched lower edge 48 of arm 44 is shifted such that a generally vertical plane 110 bisecting support member aspect 30' is generally parallel to, but spaced away at least the distance D from, the vertical plane bisecting guide wall 42 such that the chisel point 112 of tube 60' is coincident with plane 110. Although shown as a right lateral shift in FIGS. 6B and 6C, it will be appreciated that guide wall 42 and/or support member 30 could be offset with a left lateral shift if desired.

In use, a 7.0 mm or 7.5 mm ID orotracheal tube 60 is manually lubricated with a film of sterile, water-soluble, biocompatible lubricant such as SURGILUBE available from Altana, Inc., in Melville, N.Y. The lubricated tube 60 is placed in member 12, with tip 62 extending beyond free edge 52 of spout 50 and against wall 42. Guide 10 is inserted into the throat 72 while depressing and/or pulling tongue 74 out of the mouth 70 (such as with a separate tongue depressor, not shown) and sliding legs 32, 33 over tongue 74 until support member 30 seats behind tongue 74 such as with legs 32, 33 in valleculae 76. Slight traction is then applied to guide 10 in order to cock the epiglottis 90 into a more upright position near paired legs 32, 33 and front side 39, and to make guide wall 42 functionally contiguous with rear edge 80 of laryngeal opening 82. Tube 60 may then be readily guided into the laryngeal opening 82 by pushing on the proximal end 98 of tube 60 such that the tube slides off of spout 50 over top of epiglottis 90 and downward along guide wall 42. Continued pushing on tube 60 causes the medial portion 94 of tube 60 to rotate over free edge 52 of spout 50 into a more vertical orientation, and then to enter the laryngeal opening 82 and trachea, as discussed above. Once the distal end 62 of tube 60 has been advanced to the desired depth in trachea 96, guide 10 may be pulled back over tube 60, and then laterally disengaged from tube 60 through slot 49. Tube 60 is then secured to the patient in the conventional manner By virtue of the foregoing, there is thus provided a blind intubation guide that advantageously employs the features of my prior guides whereby to safely and easily intubate a patient but without the problem of catching on the epiglottis.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. For example, support portion legs 32, 33 may be eliminated so as to provide a generally straight surface that sits atop the median glosso-epiglottic fold (not numbered) between valleculae 76. Further, guide 10 may be provided with an endoscope (i.e., a laryngoscope) viewing system by placement of one or more channels (not shown) through guide 10 and terminating in one or more openings (also not shown) in guide wall 42 as described in my '805 patent, or with an endoscope viewing system as described in my U.S. patent application entitled "Endoscope Viewing System with Orotracheal Introducing Guide", Ser. No. 08/819,782 filed Mar. 18, 1997, the disclosure of which in its entirety is incorporated herein by reference. Also, to facilitate ease of use of tube 60, the distal tip 62 may be advantageously provided with a partial posterior bevel and curved anterior lip as described in my U.S. patent application entitled "Endotracheal Tube", Ser. No. 08/819,783 filed Mar. 18, 1997, the disclosure of which is also incorporated herein by reference in its entirety. The invention in its broader aspects is, therefore, not limited to the specific details, representative apparatus and method, and illustrative examples shown and described. Accordingly, departures may be made from such details without departing from the spirit or scope of the general inventive concept.

Having described the invention, what is claimed is:

1. An intubation guide comprising:
   a generally horizontal aft member;
   a generally vertical support member depending from a distal end of the aft member;
   a generally vertical guide wall spaced forwardly of the support member; and
   a spout extending from the aft member beyond the support member toward the guide wall.

2. The intubation guide of claim 1 wherein the aft member, support member, and spout meet at a junction and wherein the guide wall has an upper edge spaced below the level of the junction.

3. The intubation guide of claim 1 further comprising a side arm interconnecting the guide wall and aft member.

4. The intubation guide of claim 3 wherein the side arm has an arched lower edge.

5. The intubation guide of claim 3, the spout having a side edge adjacent the side arm.

6. The intubation guide of claim 5, the spout side edge being interconnected with the side arm.

7. The intubation guide of claim 3 wherein the aft member, support member, and spout meet at a junction and wherein the guide wall has an upper edge spaced below the level of the junction.

8. The intubation guide of claim 1 wherein the spout has a concave cross-section.

9. The intubation guide of claim I further comprising a side arm interconnecting the guide wall and the support member.

10. The intubation guide of claim 1 wherein the guide wall has a concave cross-section.

11. The intubation guide of claim 10, the guide wall and support member being in confronting relationship.

12. The intubation guide of claim 10 wherein a generally vertical first plane bisects the guide wall and a generally vertical second, generally parallel plane bisects the support member, the guide wall and support member being laterally offset relative to one another such that the first and second planes are spaced apart.

13. The intubation guide of claim 1 wherein a generally vertical first plane is coincident with a midline axis of the aft member and a generally vertical second, generally parallel plane bisects the support member, the support member being laterally offset relative to the aft member such that the first and second planes are spaced apart.

14. An intubation guide comprising:
   an aft tongue-depressing member;
   a support member depending from the aft member and extending in a direction generally transverse thereto;
   a guide wall spaced from the aft member and confronting the support member; and
   an extended tube-support extending from the aft member and beyond the support member toward the guide wall to a free distal edge spaced from both the support member and the guide wall.

15. The intubation guide of claim 14 wherein the support member and the guide wall define a tube-receiving space therebetween and which is unobstructed from above save for the extended tube-support over the free distal edge of which an orotracheal tube may rotate.

16. The intubation guide of claim 14 further comprising a side arm interconnecting the guide wall and aft member.

17. The intubation guide of claim 16 wherein the side arm has an arched lower edge.

18. The intubation guide of claim 16, the spout having a side edge adjacent the side arm.

19. The intubation guide of claim 18, the spout side edge being interconnected with the side arm.

20. The intubation guide of claim 14 wherein the aft member, support member, and spout meet at a junction and wherein the guide wall has an upper edge spaced below the level of the junction.

21. The intubation guide of claim 14 wherein the spout has a concave cross section.

22. The intubation guide of claim 14 further comprising a side arm interconnecting the guide wall and support member.

23. The intubation guide of claim 14 wherein the guide wall has a concave cross-section.

24. The intubation guide of claim 23, the guide wall and support member being in confronting relationship.

25. The intubation guide of claim 23 wherein a generally vertical first plane bisects the guide wall and a generally vertical second, generally parallel plane bisects the support member, the guide wall and the support member being laterally offset relative to one another such that the first and second planes are spaced apart.

26. The intubation guide of claim 14 wherein a generally vertical first plane is coincident with a midline axis of the aft member and a generally vertical second, generally parallel plane bisects the support member, the support member being laterally offset relative to the aft member such that the first and second planes are spaced apart.

27. A method of inserting an orotracheal tube into a laryngeal opening without the tube catching on an epiglottis in a patent's throat comprising:
   seating a guide member in the throat over the patient's tongue with an extended portion of the member effectively overhanging the epiglottis and a guide wall of the member disposed to define a pathway aimed into the laryngeal opening;
   passing the tube over the extended portion of the member whereby to clear the epiglottis; and
   continuing to pass the tube against the guide wall of the member whereby to guide a tip of the tube into the laryngeal opening.

28. The method of claim 27 further comprising partially rotating the tube over a free edge of the extended portion of the member.

29. The method of claim 27 further comprising removing the member from the throat without removing the tube.

30. The method of claim 29 comprising laterally disengaging the member from the tube.

* * * * *